United States Patent [19]

Scholz

[11] Patent Number: 4,740,471
[45] Date of Patent: * Apr. 26, 1988

[54] KARL FISCHER TITRATION AGENT AND METHOD

[75] Inventor: Eugen Scholz, Garbsen, Fed. Rep. of Germany

[73] Assignee: Riedel-De Haen Aktiengesellschaft, Frankfurt am Main, Fed. Rep. of Germany

[*] Notice: The portion of the term of this patent subsequent to Jan. 31, 2001 has been disclaimed.

[21] Appl. No.: 558,113

[22] Filed: Dec. 5, 1983

Related U.S. Application Data

[60] Continuation of Ser. No. 412,214, Aug. 27, 1982, Pat. No. 4,429,048, which is a division of Ser. No. 210,857, Nov. 26, 1980, Pat. No. 4,378,972.

[30] Foreign Application Priority Data

Mar. 5, 1980 [DE] Fed. Rep. of Germany ....... 3008421
Oct. 20, 1980 [DE] Fed. Rep. of Germany ....... 3039511

[51] Int. Cl.$^4$ ............................................. G01N 33/18
[52] U.S. Cl. ...................................... 436/42; 204/1 T
[58] Field of Search ....................... 436/39, 42, 41, 40; 204/1 T

[56] References Cited

U.S. PATENT DOCUMENTS

| | | | |
|---|---|---|---|
| 2,967,155 | 1/1961 | Blomgren et al. | 436/42 |
| 3,656,907 | 4/1972 | Delmonte | 436/42 |
| 3,661,797 | 5/1972 | Meloan et al. | 436/42 |
| 4,005,983 | 2/1977 | Dahms | 436/42 |
| 4,378,972 | 4/1983 | Scholz | 436/42 |
| 4,385,124 | 5/1983 | Verbeek et al. | 436/42 |
| 4,429,048 | 1/1984 | Scholz | 436/42 |

OTHER PUBLICATIONS

Johansson, Analytical Chemistry, vol. 28, No. 7, 1166–1168, (1956).
Smith et al., J. Am. Chem. Soc., vol. 61, 2407–2412, (1939).
Verhoff et al., Analytica Chimica Acta, vol. 94, 395–403, (1977).

Primary Examiner—Barry S. Richman
Assistant Examiner—Robert J. Hill, Jr.
Attorney, Agent, or Firm—Curtis, Morris & Safford

[57] ABSTRACT

For the titrimetric determination of small amounts of water, a Karl Fischer reagent is used which contains sulfur dioxide, iodine and a nitrogen base as essential components. The use of specific nitrogen bases in place of pyridine, which is conventionally used, is advantageous. Particularly suitable are selected aliphatic amines and nitrogen-containing heterocyclic compounds, especially imidazoles. The pyridine-free titration agent is distinguished by high storage stability and can be used as a bicomponent or monocomponent reagent.

9 Claims, 1 Drawing Sheet

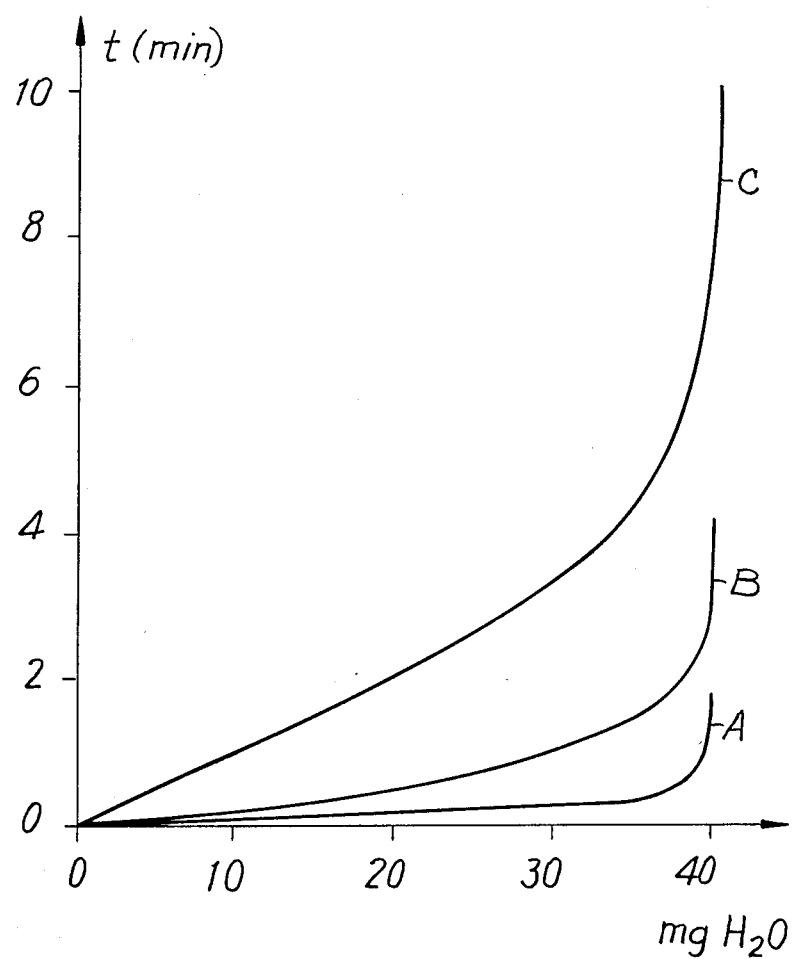

KARL FISCHER TITRATION AGENT AND METHOD

This application is a continuation of application Ser. No. 412,214 filed Aug. 27, 1982 now U.S. Pat. No. 4,429,048 issued Jan. 31, 1984, which is a divisional of application Ser. No. 210,857 filed Nov. 26, 1980, now U.S. Pat. No. 4,378,972 issued Apr. 5, 1983.

The invention provides a titration agent containing an amine, sulfur dioxide and iodine, and a method for using same for determining the water content of solid substances or liquids.

As is known, the titrimetric determination of the water content in liquids and solids was developed by Karl Fischer. This method is based on the oxidation of sulfur dioxide by iodine in the presence of water according to the following scheme:

$$2H_2O + SO_2 + I_2 \rightleftharpoons H_2SO_4 + 2HI,$$

Usually the reaction is carried out in anhydrous methanol using a reagent consisting of a solution of 790 g of pyridine, 192 g of liquid sulfur dioxide and 254 g of iodine in 5 liters of anhydrous methanol (see Angew. Chemie Vol. 48 (1935), 394). Since this solution is not stable on storage, a bicomponent reagent is generally used. Such a reagent consists of a solution of sulfur dioxide and pyridine in methanol and a solution of iodine in methanol.

It is also known that other nitrogen bases can be used instead of pyridine, for example quinoline, aniline, dimethylaniline, tri-n-butylamine and triethanolamine (see J. Amer. Chem. Soc. 1939, 2407), but do not bring about satisfactory results. Other amines intended for replacing the pyridine are ethanolamine and hexamethylene-tetramine. However, these amines are said to have the disadvantage of showing no stable titration point or causing troublesome precipitations (see Analytic. Chem. Vol. 28 (1956), 1166). The Karl Fischer reagent so modified served for determining the water content in oxidants, reducing agents and amines.

It is the object of the invention to provide a reagent suitable for determining small amounts of water, which instead of pyridine contains a substantially nontoxic amine, and is stable on storage.

The invention provides a titration agent containing an amine, sulfur dioxide and iodine, wherein the amine is (a) an aliphatic amine optionally containing 1, 2 or 3 oxygen atoms, the molar ratio of amine to sulfur dioxide being from 0.5:1 to 1.3:1; or (b) a five- or six-membered, optionally substituted, heterocyclic compound having at least 2 hetero-atoms, 1 hetero-atom at least being a nitrogen atom.

An aliphatic amine for use in the titration agent as amine base (a) is cyclic (alicyclic) or, preferably, acyclic. It may have 1, 2 or 3 oxygen atoms, preferably in the form of hydroxy groups. Especially suitable is an acyclic primary amine having from 2 to 6 carbon atoms and optionally 1, 2 or 3 hydroxy groups. Suitable amines are for example: morpholine, piperidine, piperazine, n-propylamine, isopropylamine, diethylamine, triethylamine, dimethylamino-propylamine, ethanolamine, diethanolamine, triethanolamine, tris(hydroxymethyl)-aminomethane or guanidine. The molar ratio of amine to sulfur dioxide is preferably in the range of from 0.8:1 to 1.2:1.

A heterocyclic compound for use in the titration agent as amine base (b) has five or six ring members and is optionally substituted, preferably by 1, 2 or 3 alkyl radicals having from 1 to 4 carbon atoms, or by 1, 2 or 3 phenyl radicals or a benzo group; the heterocyclic compound contains at least 2, preferably 2 or 3, hetero-atoms, one of which at least is a nitrogen atom. Especially suitable is a five-membered, optionally substituted, heterocyclic compound having 2 nitrogen atoms as hetero-atoms. The molar ratio of heterocyclic compound to sulfur dioxide is generally in the range of from 10:1 to 0.3:1, preferably 2:2 to 0.5:1.

As the heterocyclic compound, imidazole or a derivative thereof is especially suitable. Preferred, however, is a compound of the formula

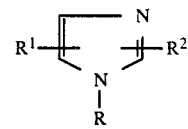

in which R, $R^1$ and $R^2$, being identical or different, each represent a hydrogen atom, a lower alkyl radical having preferably from 1 to 4 carbon atoms, or a phenyl radical.

Examples of heterocyclic compounds to be used in accordance with the invention are above all: imidazole, 1-methylimidazole, 1-ethylimidazole, 1-propylimidazole, 1-butylimidazole, 2-methylimidazole, 2-ethylimidazole, 2-propylimidazole, 2-butylimidazole, 4-methylimidazole, 4-butylimidazole, 1,2-dimethylimidazole, 1,2,4-trimethylimidazole, 1-phenylimidazole, 2-phenylimidazole and benzimidazole, furthermore imidazoline, 2-methylimidazoline (lysidine), 2-phenylimidazoline, and thiazole, 2-methylthiazole, 2-ethylthiazole, 4-methylthiazole, 4-ethylthiazole, 2-phenylthiazole, 4-phenylthiazole, benzothiazole, pyrimidine, 4-methylpyrimidine, 4-ethylpyrimidine, 1,3,5-triazine and 1,2,4-triazine.

As a solvent for the reactants of the titration agent of the invention, an anhydrous low molecular weight alcohol is used, preferably methanol or ethyleneglycol monomethyl ether, in an amount of from 2 to 50, preferably 5 to 20 mols (relative to 1 mol of amine).

The sulfur dioxide may alternatively be use in admixture with an acid, preferably a carboxylic acid with the molar ratio of sulfur dioxide to acid being from 20:1 to 1:5, preferably 2:1 to 1:2. Suitable acids are for example formic, oxalic, sulfuric, hydroiodic, and especially acetic acid.

The titration agent of the invention is prepared by dissolving the amine, the sulfur dioxide and the iodine in the alcohol, optionally with cooling to a temperature of from 15° to 50° C., preferably 20° to 40° C. The amount of amine is from 0.1 to 10, preferably 0.5 to 5, mols, that of sulfur dioxide from 0.1 to 10, preferably 0.5 to 3, mols, and that of iodine from 0.01 to 3, preferably 0.1 to 1, mol (each relative to 1 liter of solution). The solution is prepared according to known methods with exclusion of atmospheric moisture and with the use of purified starting materials.

The titration agent of the invention is excellently suitable for determining small amounts of water according to the Karl Fischer method. Thus, the invention provides a method for quantitative determination of small amounts of water by means of a reagent containing an amine, sulfur dioxide and iodine, which comprises using the titration agent of the invention as the reagent.

By means of the titration agent of the invention, the water content of solid or liquid substances is determined, for example that of inorganic salts, organic solvents, fats, oils, food, or pharmaceutical products.

The titration agent of the invention is distinguished by a high stability on storage. It is suitable for use as bicomponent reagent as well as monocomponent reagent. In the form of bicomponent reagent, its storage stability is at least 12 months, and at least 2 years when using the amine base (b). In the form of the monocomponent reagent, it is stable for about 3 weeks, and about 1 year when using the amine base (b). A special advantage of the titration agent of the invention resides in the fact that it allows a high reaction speed (see the Examples of Application). Furthermore, the titration agent is distinguished in that the end point of titration is visually well recognizable by the change in color from colorless to brown. When using the agent in commercial automatic titration equipment with voltametric indication or dead-stop indication, very stable end points are obtained, thus ensuring high precision of the resulting water content data. The titration agent is also suitable for use as an electrolyte in the coulometric water content determination.

BRIEF DESCRIPTION OF THE DRAWINGS

The following examples illustrate the invention. The course of the titration according to the Examples of Application (b), (c) and (d) is recorded by a commercial automatic titration apparatus. The accompanying drawing shows the curves obtained: curve A=titration according to Example of Application (b), curve B=titration according to Example of Application (c), and curve C=titration according to Example of Application (d) (Comparative Example).

EXAMPLE 1

(a) 420 ml of methanol are mixed with 250 g (2.87 mols) of morpholine, and 190 g (2.97 mols) of sulfur dioxide are introduced into the mixture with cooling to a temperature of 35° to 40° C. (solution A). The molar ratio of amine to $SO_2$ is 0.97:1.

(b) 85 g (0.67 mol) of iodine are dissolved in 1 liter of methanol (solution B).

(c) The solutions A+B form a bicomponent reagent. Solution A is added to the test solution, and titration is carried out with solution B.

EXAMPLE 2

(a) 56 g (0.87 mol) of sulfur dioxide are first introduced into 500 mol of methanol with cooling to 50° C., and 61 g (0.50 mol) of tris-(hydroxymethyl)aminomethane are then added to the mixture (solution A). The molar ratio of amine to $SO_2$ is 0.57:1.

(b) Solution B is identical with solution B of Example 1.

EXAMPLE 3

(a) 96 g (1.50 mols) of liquid sulfur dioxide are added to a solution of 100 g (1.69 mol) of n-propylamine in 600 ml of methanol, the temperature of the mixture being maintained by cooling at 35° to 40° C. (solution A). The molar ratio of amine to $SO_2$ is 1.12:1.

(b) Solution B is identical with solution B of Example 1.

EXAMPLE 4

(a) 157 g (1.49 mols) of diethanolamine, 60 g (1.0 mol) of acetic acid and 49 g (0.77 mol) of liquid sulfur dioxide are added one after the other to 800 ml of methanol, the temperature of the mixture being maintained by cooling at 30° to 35° C. (solution A). The molar ratio of amine to $SO_2$ is 0.84:1.

(b) Solution B is identical with solution B of Example 1.

EXAMPLE 5

A solution of 85 g (0.67 mol) of iodine in 1 liter of methanol is mixed with a solution of 157 g (1.49 mols) of diethanolamine, 60 g (1.0 mol) of acetic acid and 49 g (0.77 mol) of liquid sulfur dioxide in 800 ml of methanol. The molar ratio of amine to $SO_2$ is 0.84:1. The monocomponent reagent obtained can be used for 30 days.

EXAMPLE 6

157 g (1.49 mols) of diethanolamine, 92 g (1.43 mols) of liquid sulfur dioxide and 85 g (0.67 mol) of iodine are added one after the other to 820 ml of ethyleneglycol monomethyl ether, the temperature of the mixture being maintained by cooling at 30° C. The molar ratio of amine to $SO_2$ is 1.03:1. The monocomponent reagent obtained can be used for 1 year.

EXAMPLE 7

(a) 200 g of 2-aminothiazole (2 mols) are dissolved in 550 ml of methanol. Subsequently, with constant cooling to 15° to 20° C., 130 g of gaseous sulfur dioxide (2.03 mols) are introduced (solution A). The molar ratio of thiazole to $SO_2$ is 0.98:1.

(b) 85 g (0.67 mol) of iodine are dissolved in 1 liter of methanol (solution B).

(c) The solutions A+B form a bicomponent reagent. Solution A is added to the test solution, while titration is carried out using solution B.

EXAMPLE 8

(a) 120 g (1.86 mols) of sulfur dioxide are first introduced into 700 ml of methanol with cooling to a temperature of 20° C. Subsequently, 300 g (3.65 mols) of 2-methyl-imidazole are added with agitation and cooling in such a slow manner that the temperature does not exceed 30° C. The molar ratio of imidazole to $SO_2$ is 1.96:1.

(b) Solution B is identical with solution B of Example 7.

EXAMPLE 9

204 g (3 mols) of imidazole are dissolved in 700 g of ethyleneglycol-monomethyl ether. Subsequently, 128 g (2 mols) of sulfur dioxide are introduced, while the temperature is maintained with cooling at 25° to 30° C. Thereafter, 100 g (0.8 mol) of iodine are added. The monocomponent reagent so obtained can be used for 1 year.

EXAMPLES OF APPLICATION (a) 20 ml of methanol containing 40 mg of water is titrated with the titration agent obtained according to Example 3 in a commercial automatic titration apparatus. The titration is terminated after 140 seconds.

(b) 20 ml of methanol containing 40 mg of water is titrated with the titration agent obtained according to Example 8. Titration is terminated after 80 seconds (see curve A of the accompanying drawing). The end point of the titration can also be determined visually, because it is indicated by a color change of colorless to brown.

(c) 40 mg of water are titrated with a solution according to Example 9 in a titration apparatus. Titration is terminated after 190 seconds, and attains exactly the value of 40 mg of water, which indication remains unchanged for a further 10 minutes (see curve B). (d) Test (a) is repeated with a known Karl Fischer reagent which, per liter of ethyleneglycol-monomethyl ether, contains 250 g (3.16 mols) of pyridine, 90 g (1.40 mols) of sulfur dioxide and 140 g (1.10 mols) of iodine. Titration is possible only with the use of a commercial automatic titration apparatus, because it does not show any satisfactory change in color at the equivalent point. Titration time is 545 seconds (see curve C); the end point does not remain constant.

(e) Test (a) is repeated with a known Karl Fischer reagent which per liter of methanol contains 700 g (8.85 mols) of pyridine, 81 g (1.27 mols) of sulfur dioxide and 130 g (1.02 mols) of iodine, and which has a molar ratio of amine to $SO_2$ of 7:1. Titration time is 350 seconds.

What is claimed is:

1. A titration agent consisting essentially of an amine, sulfur dioxide, iodine and a solvent, wherein the amine is a primary or secondary aliphatic amine and the molar ratio of amine to sulfur dioxide is from 0.5:1 to 1.3:1.

2. The titration agent of claim 1, wherein the amine is diethanolamine.

3. A titration agent consisting essentially of an amine, sulfur dioxide, iodine and a solvent, wherein the amine is a primary or secondary aliphatic amine having 1, 2 or 3 oxygen atoms and the molar ratio of amine to sulfur dioxide is from 0.5:1 to 1.3:1.

4. The titration agent of claim 3, wherein the oxygen atoms are present in the form of hydroxy groups.

5. The titration agent of claim 1 or 3, wherein the solvent is an anhydrous low-molecular weight alcohol.

6. The titration agent of claim 1 or 3, wherein the solvent is present in an amount of from 2 to 50 mols, relative to 1 mol of amine.

7. The titration agent of claim 1 or 3, wherein the molar ratio of amine to sulfur dioxide is from 0.8:1 to 1.2:1.

8. The titration agent of claim 1 or 3, wherein the sulfur dioxide is in admixture with an acid in a molar ratio of sulfur dioxide to acid of from 20:1 to 1:5, said acid being sulfuric acid, hydroiodic acid or a carboxylic acid.

9. A method for the quantitative determination of water in a substance which comprises contacting the substance with the titration agent of claims 1 or 3 using the Karl Fischer method.

* * * * *

UNITED STATES PATENT AND TRADEMARK OFFICE
CERTIFICATE OF CORRECTION

PATENT NO. : 4,740,471

DATED : April 26, 1988

INVENTOR(S) : Eugen Scholz

It is certified that error appears in the above-identified patent and that said Letters Patent is hereby corrected as shown below:

Column 2, line 12, "2:2 to 0.5:1 should be --2:1 to 0.5:1--.

Signed and Sealed this

Third Day of October, 1989

Attest:

DONALD J. QUIGG

Attesting Officer

Commissioner of Patents and Trademarks